(12) United States Patent
Reed et al.

(10) Patent No.: US 7,389,693 B2
(45) Date of Patent: Jun. 24, 2008

(54) METHODS AND APPARATUS FOR POROSITY MEASUREMENT

(75) Inventors: Francis Alexander Reed, Princetown, NY (US); Thomas James Batzinger, Burnt Hills, NY (US)

(73) Assignee: General Electric Company, Schenectady, NY (US)

( * ) Notice: Subject to any disclaimer, the term of this patent is extended or adjusted under 35 U.S.C. 154(b) by 201 days.

(21) Appl. No.: 11/355,217

(22) Filed: Feb. 15, 2006

(65) Prior Publication Data

US 2007/0186655 A1  Aug. 16, 2007

(51) Int. Cl.
  *G01N 9/00* (2006.01)
(52) U.S. Cl. .............................. 73/629; 73/597; 73/599; 73/602
(58) Field of Classification Search .................... 73/620, 73/599, 600, 602, 597, 618, 629, 633, 644
  See application file for complete search history.

(56) References Cited

U.S. PATENT DOCUMENTS

| | | | |
|---|---|---|---|
| 6,684,701 B2 * | 2/2004 | Dubois et al. .................. | 73/579 |
| 7,010,980 B2 * | 3/2006 | Meier ........................... | 73/602 |
| 7,086,285 B2 * | 8/2006 | Reed ............................. | 73/629 |
| 2007/0017297 A1 * | 1/2007 | Georgeson et al. ............. | 73/801 |

OTHER PUBLICATIONS

H. Jeong et al., "Experimental Analysis of Porosity-Induced Ultrasonic Attenuation and Velocity Change in Carbon Composites," Ultrasonics, 33(3):195-203 (1995).

Nair, et al., "Porosity Estimation Using the Frequency Dependence of the Ultrasonic Attenuation," J. of Nondestructive Eval., 8(1):13-26 (1989).

Reed, et al., "Porosity Measurement in Composites Using Ultrasonic Attenuation Methods," Rev. of Progress in Quantitative Nondestructive Eval., vol. 12, pp. 1265-1272 (1993).

Krautkramer, et al., "Ultrasonic Testing of Materials," 3d. Ed., Springer-Verlag, pp. 23-26 (1983).

Krautkramer, et al., "Ultrasonic Testing of Materials," 3d. Ed., Springer-Verlag, pp. 90-96 (1983).

* cited by examiner

*Primary Examiner*—Hezron E. Williams
*Assistant Examiner*—Jacques M. Saint-Surin
(74) *Attorney, Agent, or Firm*—Armstrong Teasdale LLP

(57) ABSTRACT

A method for non-destructively inspecting a composite structure with a single ultrasonic transducer includes determining a calibration amplitude of ultrasonic transmissions emitted by the single ultrasonic transducer to a reflector in a fluid-filled immersion tank and received back at the single ultrasonic transducer. The method also includes inserting the composite structure into the fluid-filled immersion tank between the reflector and the single ultrasonic transducer. In addition, the method includes scanning the composite structure with the single ultrasonic transducer to measure ultrasonic amplitudes for sound waves traveling through the composite structure, reflecting off the reflector plate and then traveling back through the structure to the single ultrasonic transducer. The measured ultrasonic amplitudes are corrected using the calibration amplitude and other measured transmission losses, and the corrected ultrasonic amplitudes are utilized to generate either or both a digital image showing porosity or a measurement of porosity of the composite structure.

20 Claims, 5 Drawing Sheets

METHODS AND APPARATUS FOR POROSITY MEASUREMENT

BACKGROUND OF THE INVENTION

This invention relates generally to methods and apparatus for nondestructively measuring porosity in composite structures.

The identification of internal flaws in large structures is critical to the safe use of these structures. For metal structures, the identification and characterization of melt-related inclusions and cracks are critical for lifing these parts. The inspection of large metal components led to the development of sophisticated technologies for detecting surface and volumetric defects. These technologies include x-ray, penetrant, and ultrasonic methods.

New product designs and manufacturing methods can create different types of defects than those generated during the manufacture of large metal structures. The design of new structures based on polymer matrix composites is one example of these new technologies. Composite structures have some unique flaws relating to the manufacturing process which do not exist with the manufacture of metallic structures. One of these flaw types is volumetric porosity. Undetected porosity can lead to early failures of critical components.

One known method for measuring porosity in composite structures is the use of acid digestion. With acid digestion, the weight percent of matrix material and fiber material are measured separately by using acid to dissolve one of the constituents. Using these data plus mass density information for the separate materials, the percent porosity can easily be determined. However, acid digestion methods are destructive because the composite must be dissolved in order to measure the volume of porosity. Acid digestion is valuable as a process control tool where either entire parts or sections of parts can be sacrificed to measure the capability of the manufacturing process. For most critical components for which safe operation is dependent on each component working properly, this destructive testing method cannot provide the needed level of porosity detection to assure safe operation. The actual structures must be measured.

Several researchers have studied the use of sound attenuation to estimate the porosity content in composites [1,2,3]. Nair, Hsu, and Rose [1] calculated the acoustic scattering caused by pores in a composite structure. They suggest the use of attenuation slope measurements for estimating porosity. They also provide experimental results that show an agreement between the experimental estimation of porosity, the theoretical calculation of the attenuation based on scattering theory, and actual porosity measurements collected using acid digestion methods, Jeong and Hsu [2] continued work on the experimental analysis of attenuation slope measurements to estimate porosity. Jeong et al developed an immersion-based attenuation measurement technique that corrected for transducer diffraction and sound transmission losses. The researchers also identified that the attenuation slope measurement was sensitive to the shape or aspect ratio of the pores. This leads to three different coefficients for estimating porosity content from attenuation slope dependent on the construction technique for the composite structure.

Reed, Batzinger, Reed, and Jonsson [3] identified additional corrections needed for attenuation measurements made using focused immersion transducers. A correction for the surface roughness losses and a spatial filtering method to correct for frequency-dependent focusing effects were discussed. Experimental data showed agreement between the attenuation estimation of porosity and actual values determined by destructive sectioning of the sample.

All three groups demonstrated the applicability of using ultrasonic attenuation to estimate porosity in a laboratory setting. The data generally shows agreement between ultrasonic estimates for porosity measurement and actual values based on acid digestion or sectioning.

In general, known methods require precision scanning of two transducers collecting data at a plurality of frequencies. To collect the ultrasonic information needed to analyze porosity would require two or more scans of the part depending on the attenuation slope calculation method used, a serious limitation to manufacturing productivity. Additionally, two transducers are required for these measurements with their positioning axes. Since most immersion tanks designed for metal inspection have only one transducer manipulator, new immersion tanks with two fully controllable transducer manipulators would be required to implement these methods.

Another problem with the methods developed by these three groups is that the complexity of the calibration and measurements could make the inspection difficult for non laboratory-trained technicians. The diffraction correction techniques discussed by Jeong et al [2] require sophisticated mathematical skills including complex number mathematics. The focusing correction techniques used by Reed et al [3] require spatial convolutions of attenuation images to correct for focusing effects. These calculations would make the transfer of these techniques to a manufacturing environment very difficult.

BRIEF DESCRIPTION OF THE INVENTION

Therefore, in one aspect, the present invention provides a method for non-destructively inspecting a composite structure with a single ultrasonic transducer. The method includes determining a calibration amplitude of ultrasonic transmissions emitted by the single ultrasonic transducer to a reflector in a fluid-filled immersion tank and received back at the single ultrasonic transducer. The method also includes inserting the composite structure into the fluid-filled immersion tank between the reflector and the single ultrasonic transducer. In addition, the method includes scanning the composite structure with the single ultrasonic transducer to measure ultrasonic amplitudes for sound waves traveling through the composite structure, reflecting off the reflector plate and then traveling back through the structure to the single ultrasonic transducer. The measured ultrasonic amplitudes are corrected using the calibration amplitude and other measured transmission losses, and the corrected ultrasonic amplitudes are utilized to generate a digital image porosity and/or a porosity measurement of the composite structure.

In another aspect, the present invention provides a method for non-destructively inspecting a composite structure with a single ultrasonic transducer. The method includes determining a calibration amplitude of ultrasonic transmissions emitted by the single ultrasonic transducer to a front surface of the composite structure in a fluid-filled immersion tank and received back at the single ultrasonic transducer. The method further includes inserting the composite structure into the fluid-filled immersion tank and scanning the composite structure with the single ultrasonic transducer to measure ultrasonic amplitudes for sound waves traveling through the composite structure, reflecting off a back wall of the composite structure and then traveling back through the structure to the single ultrasonic transducer. The measured ultrasonic amplitudes are corrected using the calibration amplitude and other measured transmission losses, and the corrected ultrasonic amplitudes are utilized to generate a digital image porosity and/or a porosity measurement of the composite structure.

In yet another aspect, the present invention provides an apparatus for non-destructively inspecting a composite structure with a single ultrasonic transducer. The apparatus has a single ultrasonic transducer configured to transmit and receive ultrasonic sound waves, electronic equipment configured to operate the ultrasonic transducer to generate and amplify the ultrasonic sound waves. The apparatus further includes a fluid-filled or fluid-fillable immersion tank, a scanning system configured to position the ultrasonic transducer and composite structure to obtain ultrasonic information, and a data collection system including a computer. The data collection system is configured to collect ultrasonic information and to convert said ultrasonic information into digital images. The apparatus is configured to determine a calibration amplitude of ultrasonic transmissions emitted by the single ultrasonic transducer to at least one of a reflector in a fluid-filled immersion tank and a back side of the composite structure and received back at the single ultrasonic transducer. The apparatus is also configured to scan a composite structure inserted into the fluid-filled immersion tank with the ultrasonic transducer to measure ultrasonic amplitudes for sound waves traveling through the composite structure, reflecting off the reflector plate or the back side of the composite structure and then traveling back through the structure to the ultrasonic transducer. The apparatus is further configured to correct the measured ultrasonic amplitudes using the calibration amplitude and other measured transmission losses, and utilize the corrected ultrasonic amplitudes to generate a digital image porosity and/or a porosity measurement of the composite structure.

It will be appreciated that various configurations of the present invention provide a nondestructive method for measuring the porosity content in composite structures during the manufacturing process and that this method is advantageous for designing and lifting these components. Various configurations of the present invention also measure the porosity volume in a composite structure nondestructively using readily available ultrasonic equipment. Configurations of the present invention require only one scan for ultrasonic attenuation measurement instead of multiple scans as was required for prior art techniques. Configurations of the present invention also require only one transducer, thereby simplifying calibration and inspection procedures. Method configurations of the present invention are relatively simple and straightforward requiring no unusual skills that most ultrasonic inspectors would not possess.

DETAILED DESCRIPTION OF THE INVENTION

Technical effects of the present invention include the nondestructive measurement of porosity of a composite structure and/or the generation of a digital imaging showing porosity of the composite structure.

Figure 1:
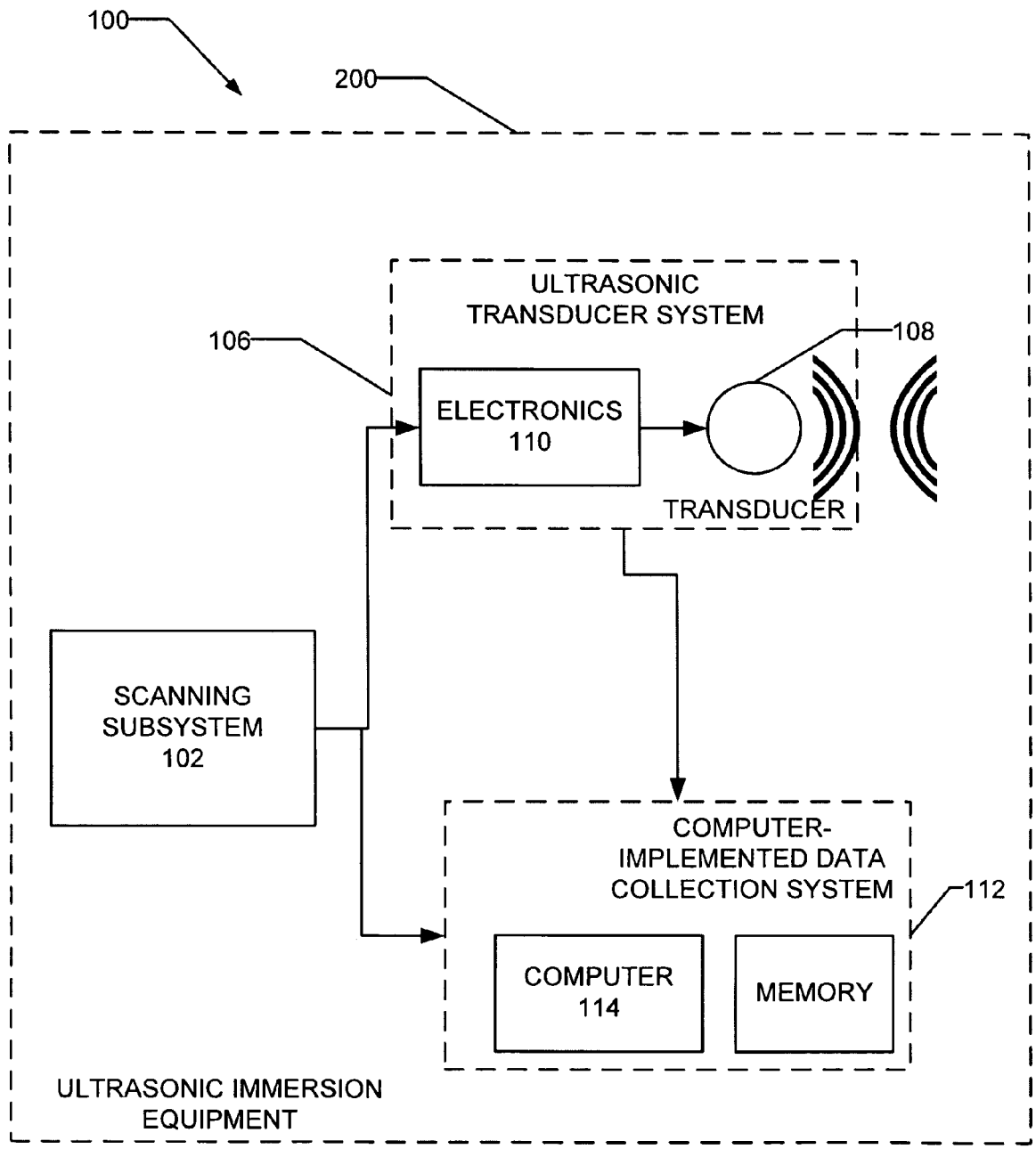
FIG. 1 is a block diagram of a configuration of ultrasonic immersion equipment suitable for use with configurations of the present invention.
Figure 2:
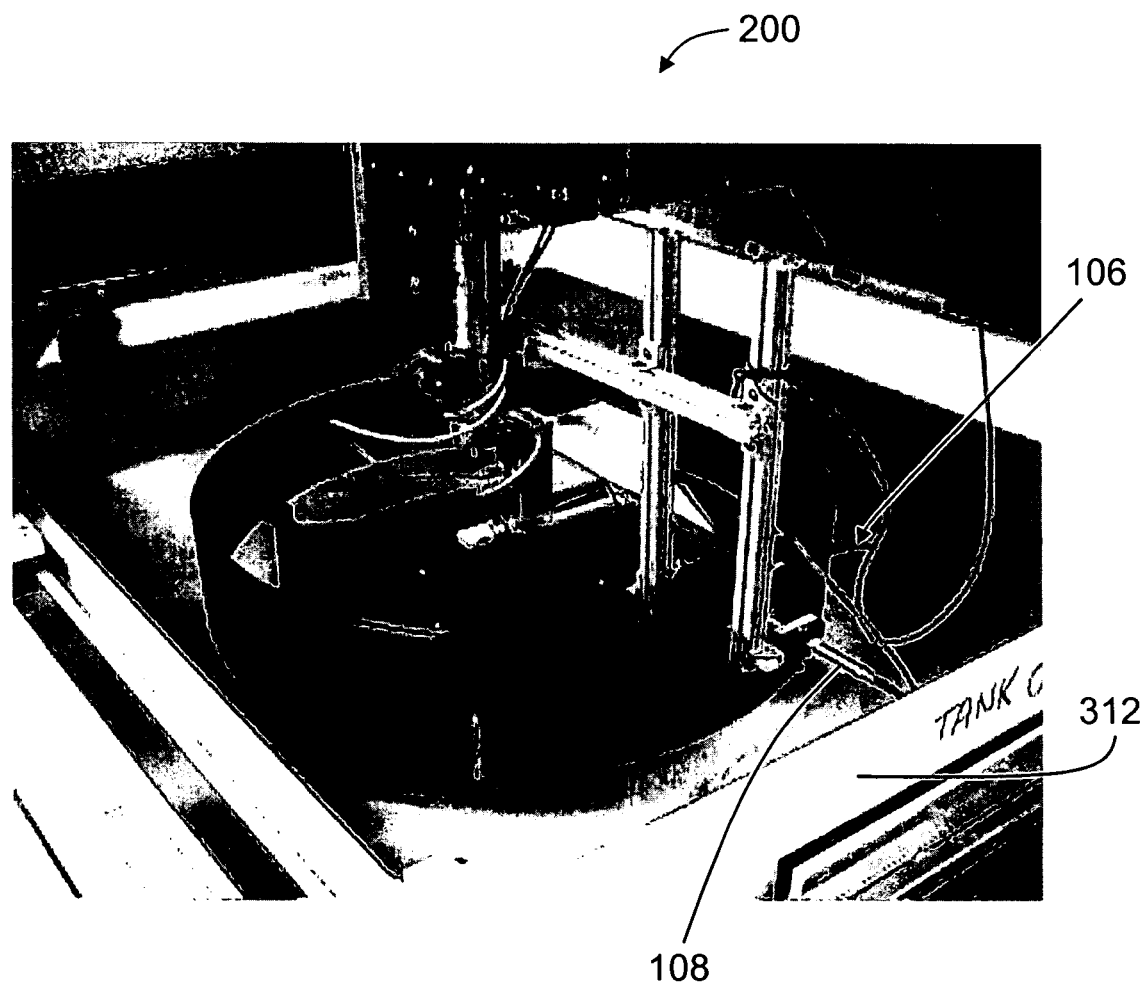
FIG. 2 is a pictorial diagram of the ultrasonic immersion equipment of FIG. 1.

Some configurations of the present mention use a porosity measurement method that uses standard ultrasonic immersion equipment similar to equipment used for inspecting metal forgings. Such equipment is readily available for use in inspecting composite structures and is manufactured by many companies, although the computer subsystems of the readily available equipment are not preconfigured as described herein. In some configurations, and referring to the example configuration block diagram 100 of FIG. 1 and the pictorial diagram of FIG. 2, there are three subsections of ultrasonic immersion equipment 200, namely (a) a scanning system 102 configured to position a transducer 108 for transmitting and collecting ultrasonic data, (b) an ultrasonic transducer system 106 having an ultrasonic transducer 108 configured to transmit and receive ultrasonic sound waves and also having electronic equipment 110 configured to generate and amplify those signals, and (c) a computer-implemented data collection system 112 including a computer 114 configured to collect ultrasonic information and to convert the collected information (i.e., data) to digital images.

Configurations of the present invention use only one transducer 108 for collecting ultrasonic signals. This single transducer 108 is used to both generate and receive ultrasonic waves, as is commonly done for metals inspection. For metals inspection, ultrasonic signals directly reflected from an internal defects are measured and characterized. However, in configurations of the present invention, different calibration methods are needed from those used for evaluating metal parts, and computer 114 is configured differently (such as by the use of appropriate software or firmware) to accommodate the calibration methods.

Instead of measuring amplitudes of ultrasonic reflections from internal defects as is performed with inspections of metal structures, porosity measurement configurations of the present invention use measurement of the attenuation of sound waves as they travel through a structure.

Figure 3:
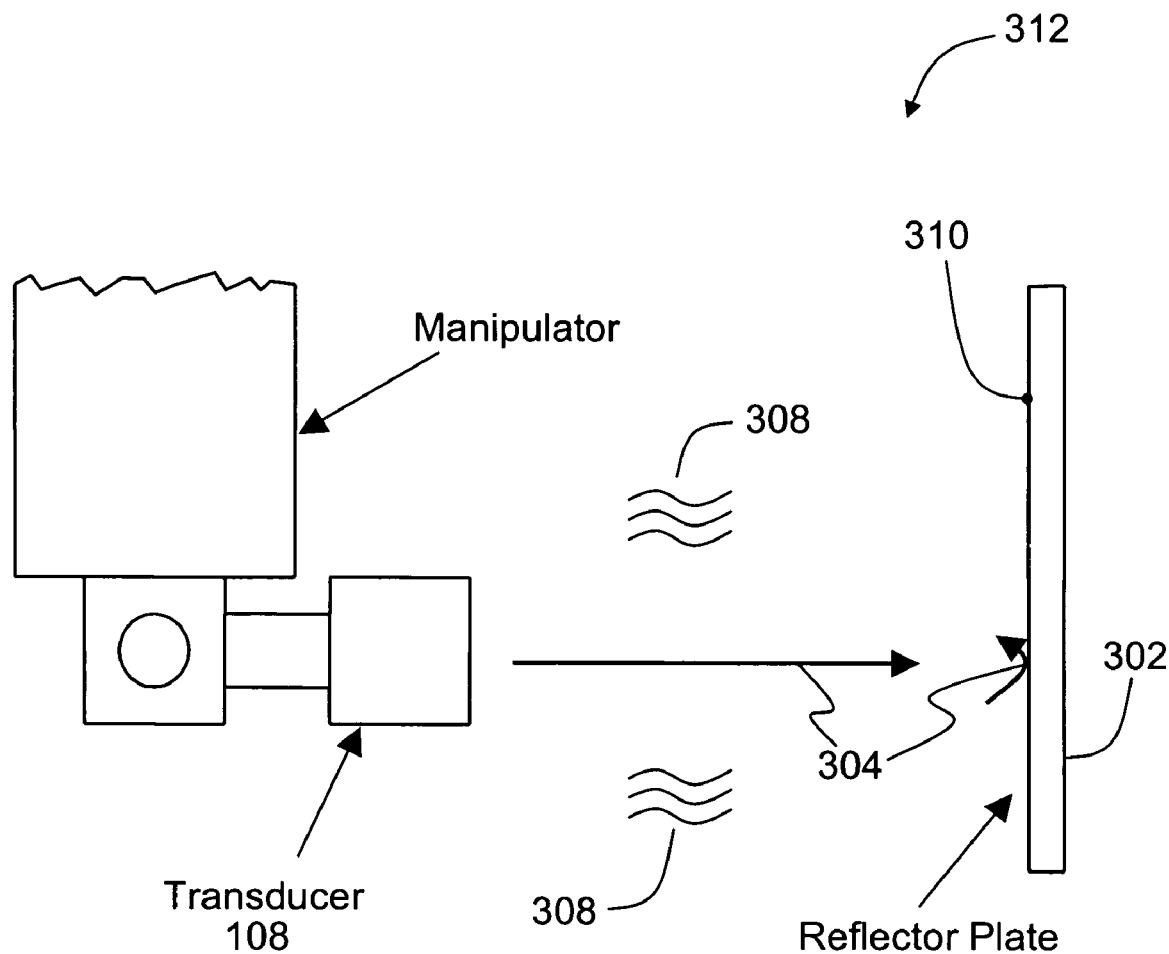
FIG. 3 is a representation of a calibration measurement method used in some configurations of the present invention.
Figure 4:
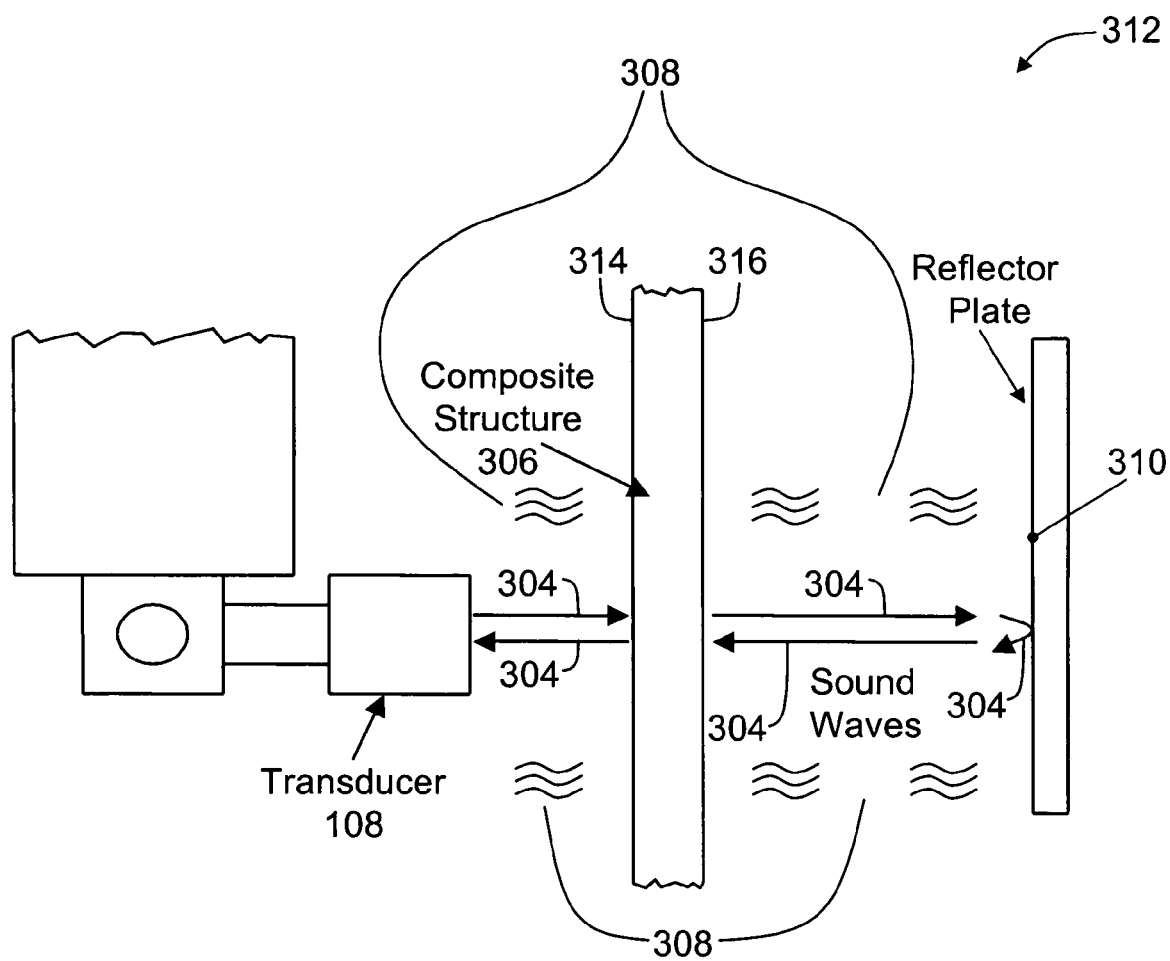
FIG. 4 is a representation of a method for evaluating a composite structure used in the configurations of the present invention represented by FIG. 3.

In some configurations of the present invention and referring to FIGS. 3 and 4, attenuation is measured using a reflector plate 302. Amplitudes of ultrasonic signals 304 are measured prior to entry into a structure 306 and after exit of structure 306. The ratio of the two measured amplitudes gives the attenuation of sound associated with traveling through structure 306.

The amplitude of ultrasonic waves 304 entering structure 306 can be determined in a calibration step by measuring reflected ultrasonic waves 304 from a reflector plate 302 and then correcting this value for transmission losses. The amplitude of waves 304 traveling through water or other immersion fluid 308 is determined by measuring the amplitude of ultrasonic waves 304 reflecting off a front surface 310 of reflector plate 302.

After these calibration data have been collected, composite structure 306 is placed in immersion tank 312 for evaluation. As transducer 108 is scanned over structure 306, the amplitudes for ultrasonic waves 304 traveling through composite structure 306, reflecting off reflector plate 302, and then traveling back through structure 306 to transducer 108 are measured and recorded. Since these waves 304 are reduced in amplitude not only by the material effects of the porosity but also by sound transmission losses associated with sound traversing the two water-composite interface surfaces 314, 316 of structure 306, the amplitude of these waves must be corrected to compensate for these transmission losses. For configurations of the present invention using reflector plate 302, the correction needed is written:

$$\text{Corrected Amplitude} = \text{Measured Amplitude} \times \left(\frac{(z_1+z_2)^2}{(4z_1z_2)}\right)^2,$$

where:

Measured Amplitude is the signal amplitude of ultrasonic wave 304 traveling through composite 306, Corrected Amplitude is the ultrasonic amplitude corrected for transmission losses, $z_1$ is the acoustic impedance of immersion fluid 308, and $z_2$ is the acoustic impedance of composite structure 306.

The derivation of this correction factor can be found in Krautkramer [4]. Since the acoustic impedance of fluid 308 (usually water) is known and the acoustic impedance of composite structure 306 is either known or measured before the inspection, this calculation is, in many configurations, a simple multiplication of collected amplitude data by a constant value.

If composite structure 306 is thick, an additional correction factor for diffraction effects may be needed. Correction by Distance Gain Size (DGS) diagram can be used in configurations in which a diffraction effect correction factor is used. DGS diagrams are available from most transducer manufacturers and arc also can be easily derived for unfocused probes or transducers 108 using generic DGS diagrams. This correction compensates for the increase in length measured in nearfield lengths that ultrasonic waves 304 travels when a composite structure 306 is introduced between reflector plate 302 and transducer 108. The travel lengths in nearfield lengths are calculated for the water path for the calibration measurement and for the water path and sound path through composite 306 for the actual composite measurement. For the composite measurement, the sound path distance in near fields is the sum of the water path distance in nearfield lengths and the travel distance in composite structure 306 in nearfield lengths. Using a DGS diagram, the drop in amplitude due to the increased path length can be directly determined from the amplitude data for the back wall or infinite reflector line [5].

The back wall gain values for both the calibration distance and the porosity measurement distance can be determined from the DGS curve. The diffraction-corrected amplitude value can be calculated as follows:

$$\text{Amplitude} = \text{Corrected Amplitude} \times 10^{\left(\frac{dBcomp - dBcal}{20}\right)},$$

Where:

Amplitude is the diffraction-corrected amplitude for sound wave traveling through the composite structure, Corrected Amplitude is the sound amplitude corrected for transmission losses calculated above, dBcomp is the gain determined using a DGS plot for a signal at the porosity measurement path length, and dBcal is the gain determined using a DGS plot for a signal at the calibration measurement path length.

For thin composite structures 306, this correction is small and can be neglected to simplify the measurement.

The attenuation can now be determined using the calibration amplitude and the composite corrected amplitude or diffraction corrected amplitude. The attenuation in decibels can be calculated as follows:

$$\alpha(dB) = -20\log_{10}\left(\frac{\text{Composite Amplitude}}{\text{Calibration Amplitude}}\right),$$

Where:

$\alpha(dB)$ is the attenuation in decibels,

Composite Amplitude is the amplitude for an ultrasonic wave 304 traveling through composite structure 306 with corrections for transmission losses and diffraction if needed, and Calibration Amplitude is the amplitude of an ultrasonic wave 304 traveling through immersion fluid 308 and reflecting off reflector plate 302.

Figure 5:
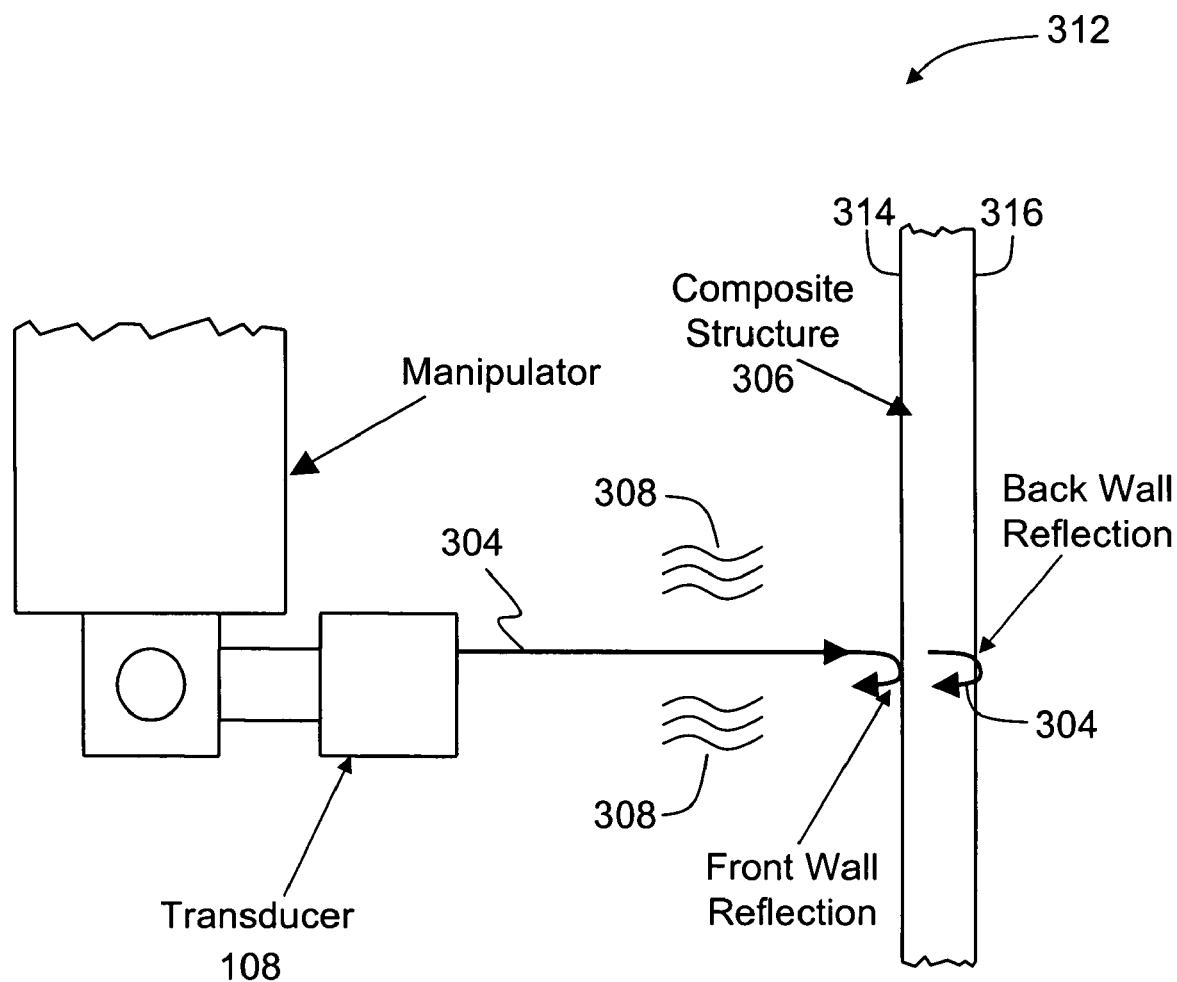
FIG. 5 is a representation of a method for calibration and for evaluating a composite structure used in some other configurations of the present invention.

In some configurations of the present invention and referring to FIG. 5, the attenuation for a composite structure 306 immersed in a fluid 308 is determined without using a reflector plate 302.

The calibration amplitude is replaced with the reflection from front surface 314 of composite structure 306 and the composite measurement amplitude is replaced with the reflection from back wall 316 of composite structure 306. The amplitude of the front surface reflection is used in some configurations to determine an ultrasonic wave amplitude entering structure 306 while the back wall amplitude is used to determine the amplitude that is transmitted through structure 306. In both of these cases, amplitudes are corrected for transmission and reflection losses. FIG. 5 shows the layout for this porosity measurement.

In some configurations, the diffraction correction for the back wall reflection is accomplished in a similar fashion to the correction performed in configurations using reflector plate 302. More specifically, the calibration distance is the distance in nearfield lengths between transducer 108 and front surface 314 of composite structure 306. The porosity measurement distance is the calibration distance in nearfield lengths plus the thickness of composite structure 306 in nearfield lengths. An equation discussed in the method described above is then used to determine the corrected back wall amplitude. This correction will only be significant for thick composite structures 306 and is not necessary for use with thin composite structures 306.

In some configurations, the attenuation for the porosity measurement is determined directly from a front surface reflection and either a back wall reflection or a diffraction-corrected back wall reflection. To perform this measurement, an equation written as follows can be used:

$$\alpha(dB) = -20\log_{10}\left(\left(\frac{\text{Back wall Amplitude}}{\text{Front wall Amplitude}}\right) \times \left(\frac{4z_1z_2}{(z_1+z_2)^2}\right)\right),$$

Where:

$\alpha(dB)$ is the attenuation in decibels,

Back wall Amplitude is the amplitude of reflected ultrasonic wave 304 from back surface 316 of composite structure 306 or the diffraction-corrected value of the back wall reflection, Front wall Amplitude is the amplitude of ultrasonic wave 304 reflected from front surface 314 of composite structure 306, $z_1$ is the acoustic impedance of immersion fluid 308, and $z_2$ is the acoustic impedance of composite structure 306.

Using the attenuation slope from the ultrasonic measurement, porosity can be estimated using an equation written:

Porosity(%)=Coefficient×Attenuation slope+offset,

Where:

Porosity is the volume percent porosity in composite structure 306 at the ultrasonic measurement location, Coefficient is a scaling term calculated either theoretically or by experimental tests, Attenuation slope is the change in attenuation per unit thickness versus frequency, and Offset is a fitting term which is equal to the porosity value for zero attenuation slope measurements.

The coefficient value has been theoretically calculated and experimentally verified [1,2,3]. For use on graphite fiber/epoxy matrix materials with unidirectional or two-dimensional lay-ups, the coefficient value is 0.45 (percent porosity× cm×MHz/dB). Values for other composite structures have been published [1,2].

The attenuation slope is the slope of a line fitted to the attenuation per unit thickness and the measurement frequency. For the coefficient term given above, the attenuation is given in decibels and the thickness is measured in centimeters. The frequency for the slope calculation is measured in megahertz (MHz). While the laboratory tests on composites collected attenuation data at multiple frequencies, for production inspections this testing has been simplified. For all the theoretical calculations and most experimental tests, there exists a known attenuation versus frequency point that can be used to calculate the attenuation slope. This point is the value of attenuation at 0.0 MHz; the value of the attenuation at this point is 0.0 dB/unit length. Using this value plus one additional attenuation value measured on the composite structure, the porosity can be estimated from the ultrasonic data. This simplification reduces the measurement time by 50% or greater when compared to previously published work.

The offset value based on published data is 0.4% porosity for unidirectional and two-dimensional ply graphite epoxy structures. Other values may be used to estimate porosity from the ultrasonic data.

This porosity data can be used to form a porosity image or map where the localized porosity in the structure can be reviewed. This additional image cannot be formed using the destructive techniques. This image can be used to determine the quality of the structure and whether the structure is acceptable for use in critical applications.

As an experiment, attenuation scans were taken of a sample graphite composite plate that were then used to estimate the volume porosity. The ultrasonic attenuation value agreed with acid digestion data from adjacent material. The two ends of the sample had porosity values on the order of 1.5% and the center of the composite is closer to 4%.

Validation of the single frequency measurement of the attenuation slope was also performed using attenuation data collected. The results of the testing showed agreement between the single frequency measurement porosity estimation and the multiple frequency measurement.

Custom imaging and porosity calculation software was developed for use with the porosity measurement system. This software performed the calculations described herein, requiring only input information such as part thickness, inspection frequency, transmission losses (4.8 dB for graphite epoxy composites), and calibration sound level. This software was successfully used to analyze composite cylinders.

Thus, it has been shown that various configurations of the present invention provide a nondestructive method for measuring the porosity content in composite structures during the manufacturing process and that this method is advantageous for designing and lifting these components. Various configurations of the present invention also measure the porosity volume in a composite structure nondestructively using readily available ultrasonic equipment. Configurations of the present invention require only one scan for ultrasonic attenuation measurement instead of multiple scans as was required for prior art techniques. Configurations of the present invention also require only one transducer, thereby simplifying calibration and inspection procedures. Method configurations of the present invention are relatively simple and straightforward requiring no unusual skills that most ultrasonic inspectors would not possess.

REFERENCES REFERRED TO IN THIS APPLICATION ARE

[1] Satish M. Nair, David K. Hsu, and James H. Rose; "Porosity Estimation Using the Frequency Dependence of the Ultrasonic Attenuation"; Journal of Nondestructive Evaluation; Vol. 8; No. 1; 1989; pages 13-26.

[2] H. Jeong and D. K. Hsu; "Experimental analysis of porosity-induced ultrasonic attenuation and velocity change in carbon composites,"Ultrasonics; Vol. 33; No. 3; 1995; pages 195-203.

[3] F. A. Reed, T. J. Batzinger, R. W. Reed, and S. Jönsson; "Porosity Measurement in Composites using Ultrasonic Attenuation Methods,"Review of Progress in Quantitative Nondestructive Evaluation, 12B, 1993.

[4] J. Kräutkramer and H. Kräutkramer, "Ultrasonic Testing of Materials"; Third Edition; Springer-Verlag; 1983; pages 23-26.

[5] J. Kräutkramer and H. Kräutkramer; "Ultrasonic Testing of Materials"; Third Edition, Springer-Verlag; 1983; pages 90-96.

While the invention has been described in terms of various specific embodiments, those skilled in the art will recognize that the invention can be practiced with modification within the spirit and scope of the claims.

What is claimed is:

1. A method for non-destructively inspecting a composite structure with a single ultrasonic transducer, said method comprising:
   determining a calibration amplitude of ultrasonic transmissions emitted by the single ultrasonic transducer to a reflector in a fluid-filled immersion tank and received back at the single ultrasonic transducer;
   inserting the composite structure into the fluid-filled immersion tank between the reflector and the single ultrasonic transducer;
   scanning the composite structure with the single ultrasonic transducer to measure ultrasonic amplitudes for sound waves traveling through the composite structure, reflecting off the reflector plate and then traveling back through the structure to the single ultrasonic transducer;
   correcting the measured ultrasonic amplitudes using the calibration amplitude and other measured transmission losses;
   utilizing the corrected ultrasonic amplitudes to generate at least one of a digital image showing porosity or a porosity measurement of the composite structure.

2. A method in accordance with claim 1 wherein said correcting the measured ultrasonic amplitudes further comprises utilizing a known acoustic impedance of the fluid and using a known or previously measured acoustic impedance of the composite material to determine a constant value with which to scale the measured ultrasonic amplitudes.

3. A method in accordance with claim 2 wherein said correcting the measured ultrasonic amplitudes further comprises applying an additional correction to compensate for an increase in length that the ultrasonic signal travels when the composite structure is introduced between the reflector and the single ultrasonic transducer.

4. A method in accordance with claim 3 wherein said applying an additional correction further comprises utilizing a distance gain size diagram to determine the additional correction.

5. A method for non-destructively inspecting a composite structure with a single ultrasonic transducer, said method comprising:
  determining a calibration amplitude of ultrasonic transmissions emitted by the single ultrasonic transducer to a front surface of the composite structure in a fluid-filled immersion tank and received back at the single ultrasonic transducer;
  inserting the composite structure into the fluid-filled immersion tank;
  scanning the composite structure with the single ultrasonic transducer to measure ultrasonic amplitudes for sound waves traveling through the composite structure, reflecting off a back wall of the composite structure and then traveling back through the structure to the single ultrasonic transducer;
  correcting the measured ultrasonic amplitudes using the calibration amplitude and other measured transmission losses;
  utilizing the corrected ultrasonic amplitudes to generate at least one of a digital image showing porosity or a porosity measurement of the composite structure.

6. A method in accordance with claim 5 wherein said correcting the measured ultrasonic amplitudes further comprises utilizing a known acoustic impedance of the fluid and using a known or previously measured acoustic impedance of the composite material to determine a constant value with which to scale the measured ultrasonic amplitudes.

7. A method in accordance with claim 6 wherein said correcting the measured ultrasonic amplitudes further comprises applying an additional correction to compensate for diffraction in the back wall reflected ultrasonic signals.

8. A method in accordance with claim 7 further comprising determining an attenuation slope for the ultrasonic signal, and utilizing the attenuation slope to estimate porosity of the composite object.

9. A method in accordance with claim 8 wherein said determining an attenuation slope for the ultrasonic signal comprises determining a slope of a line fitted to attenuation per unit thickness and measurement frequency.

10. A method in accordance with claim 8 wherein said determining an attenuation slope comprise utilizing a 0.0 dB/unit length value of attenuation at 0.0 MHz, and measuring on additional attenuation value on the composite structure.

11. An apparatus for non-destructively inspecting a composite structure with a single ultrasonic transducer, said apparatus comprising:
  a single ultrasonic transducer configured to transmit and receive ultrasonic sound waves;
  electronic equipment configured to operate said single ultrasonic transducer to generate and amplify said ultrasonic sound waves;
  a fluid-filled or fluid-fillable immersion tank;
  a scanning system configured to position said single ultrasonic transducer and composite structure to obtain ultrasonic information; and
  a data collection system including a computer, said data collection system configured to collect ultrasonic information and to convert said ultrasonic information into digital images;
  said apparatus configured to:
  determine a calibration amplitude of ultrasonic transmissions emitted by the single ultrasonic transducer to at least one of a reflector in a fluid-filled immersion tank and a back side of the composite structure and received back at the single ultrasonic transducer,
  scan a composite structure inserted into said fluid-filled immersion tank with the single ultrasonic transducer to measure ultrasonic amplitudes for sound waves traveling through the composite structure, reflecting off said one of the reflector plate or the back side of the composite structure and then traveling back through the structure to the single ultrasonic transducer;
  correct the measured ultrasonic amplitudes using the calibration amplitude and other measured transmission losses;
  utilize the corrected ultrasonic amplitudes to generate at least one of a digital image showing porosity or a porosity measurement of the composite structure.

12. An apparatus in accordance with claim 11 wherein to correct the measured ultrasonic amplitudes, said computer configured to utilize a constant value with which to scale the measured ultrasonic amplitudes.

13. An apparatus in accordance with claim 12 wherein to correct the measured ultrasonic amplitudes, said computer further configured to apply an additional correction to compensate for an increase in length that the ultrasonic signal travels when the composite structure is introduced in the fluid-filled tank between a reflector in the fluid-filled tank and the single ultrasonic transducer.

14. An apparatus in accordance with claim 13 wherein to applying an additional correction, said computer further configured to utilize a distance grain size diagram to determine the additional correction.

15. An apparatus in accordance with claim 11 wherein to determine a calibration amplitude of ultrasonic transmissions said system configured to determine a calibration amplitude emitted by the single ultrasonic transducer to a back side of the composite structure and received back at the single ultrasonic transducer; and to scan the composite structure inserted into said fluid-filled immersion tank, said apparatus configured to scan a composite structure inserted into said fluid-filled immersion tank with the single ultrasonic transducer to measure ultrasonic amplitudes for sound waves traveling through the composite structure, reflecting off said back side of the composite structure and then traveling back through the structure to the single ultrasonic transducer.

16. An apparatus in accordance with claim 15 wherein to correct the measured ultrasonic amplitudes further comprises said apparatus configured to utilize a known acoustic impedance of the fluid and using a known or previously measured acoustic impedance of the composite material to determine a constant value with which to scale the measured ultrasonic amplitudes.

17. An apparatus in accordance with claim 16 wherein to correct the measured ultrasonic amplitudes, said apparatus further configured to apply an additional correction to compensate for diffraction in the back wall reflected ultrasonic signals.

18. An apparatus in accordance with claim 17 further configured to determine an attenuation slope for the ultrasonic signal, and to utilize the attenuation slope to estimate porosity of the composite object.

19. An apparatus in accordance with claim 18 wherein to determine an attenuation slope for the ultrasonic signal, said apparatus configured to determine a slope of a line fitted to attenuation per unit thickness and measurement frequency.

20. An apparatus in accordance with claim 18 wherein to determine an attenuation slope, said apparatus configured to utilize a 0.0 dB/unit length value of attenuation at 0.0 MHz, and measuring on additional attenuation value on the composite structure.

* * * * *